United States Patent [19]

Mazurek et al.

[11] Patent Number: 5,091,483

[45] Date of Patent: Feb. 25, 1992

[54] RADIATION-CURABLE SILICONE ELASTOMERS AND PRESSURE SENSITIVE ADHESIVES

[75] Inventors: Mieczyslaw H. Mazurek; Steven S. Kantner; Charles M. Leir, all of St. Paul, Minn.; Yvan A. Bogaert, Gent, Belgium; Robert K. Galkiewicz; Audrey A. Sherman, both of St. Paul, Minn.

[73] Assignee: Minnesota Mining and Manufacturing Company, St. Paul, Minn.

[21] Appl. No.: 671,172

[22] Filed: Mar. 15, 1991

Related U.S. Application Data

[63] Continuation of Ser. No. 411,410, Sep. 22, 1989, abandoned.

[51] Int. Cl.$^5$ ............................................ C08G 77/00
[52] U.S. Cl. ........................................ 525/477; 525/474; 528/41; 528/38; 528/24; 528/21; 528/26; 528/12
[58] Field of Search ............... 528/41, 38, 24, 12, 528/21, 26; 525/474, 477

[56] References Cited

U.S. PATENT DOCUMENTS

| | | | |
|---|---|---|---|
| 3,775,452 | 11/1973 | Karstedt | 260/429 R |
| 4,153,641 | 5/1979 | Deichert et al. | 260/827 |
| 4,293,397 | 10/1981 | Sato et al. | 204/159.13 |
| 4,364,809 | 12/1982 | Sato et al. | 204/159.13 |
| 4,369,300 | 1/1983 | Carter et al. | 528/28 |
| 4,370,358 | 1/1983 | Nayes et al. | 427/54.1 |
| 4,503,208 | 3/1985 | Lin et al. | 528/15 |
| 4,563,539 | 1/1986 | Gornowicz et al. | 556/421 |
| 4,575,545 | 3/1986 | Nakos et al. | 526/242 |
| 4,575,546 | 3/1986 | Klemarczyk et al. | 526/245 |
| 4,591,608 | 5/1986 | Okinoshima | 522/13 |
| 4,603,086 | 7/1986 | Fujii et al. | 428/447 |
| 4,605,712 | 8/1986 | Mueller et al. | 525/474 |
| 4,640,940 | 2/1987 | Jacobine et al. | 522/99 |
| 4,675,346 | 6/1987 | Lin et al. | 522/39 |
| 4,728,571 | 3/1988 | Clemens et al. | 428/352 |
| 4,777,276 | 10/1988 | Rasmussen et al. | 556/419 |

FOREIGN PATENT DOCUMENTS

| | | |
|---|---|---|
| 170219 | 5/1986 | European Pat. Off. |
| 176894 | 12/1965 | U.S.S.R. |

OTHER PUBLICATIONS

Yu et al., J. Appl. Polym. Sci. 30, 2115 (1985).
Lewis, Rubb. Chem. Tech. 35, 1222 (1962).
R. Hatada and H. Kondo, Bull. Chem. Soc. Japan, 41 (10), 2521 (1968).
"Silicone Elastomers", Encyclopedia of Polymer Science and Engineering, 1989, vol. 15, pp. 271-308.
Synthesis of Organofluorosilicon Compounds Containing Amine Group in Organic Radical, G. B. Dmitrieva and B. A. Sokolov, Technical University of Irkutsk.
Reaction of Carboxylic Acid Fluorides and Perfluoropropylene Oxide with (Acyloxymethyl)dimethylethoxysilanes, Institute of Heteroorganic Compounds, Academy of Sciences of the U.S.S.R., Moscow, Translated from Izvestiya Akademii Nauk S.S.S.R., Seriya Khimicheskaya, No. 9, pp. 2063-2065, Sep., 1974, Original Submitted Jan. 17, 1974.
Synthesis of Silicone-, Germanium-, and Tin-Containing Styrene and a-Methylstyrene, E. A. Chernyshev, A. D. Petrov, and T. L. Krasnova, Sintez i Svoistva Monomerov, Akad, Nauk S.S.S.R., Inst. Neftekhim, Sinteza, Sb. Rabot 12-oi [Dvenadtsatoi] Konf. po Vysokomolekul, Soedin, 1962, 103-8 (Pub. 1964) (Russ), This article will follow at a later date.
Reaction of Hydrosilanes with Methacrylic Acid Esters, A. N. Grishko, S. A. Nefed'eva, T. G. Suvorova, (U.S.S.R.), Sintez Vysokomolekul, Produktov na Osnove Sapropelitov i Kremniiorgan, Soedin, 1976, (Ch. 1), 10-16 (Russ), From Ref. Zh., Khim., 1977, Abstr. No. 8ZH339, This article will follow at a later date.

Primary Examiner—Paul R. Michl
Assistant Examiner—Karen A. Hellender
Attorney, Agent, or Firm—Gary L. Griswold; Walter N. Kirn; Janice L. Dowdall

[57] ABSTRACT

A composition which is curable to an elastomer comprising:
A polymer or mixture of polymers of the formula

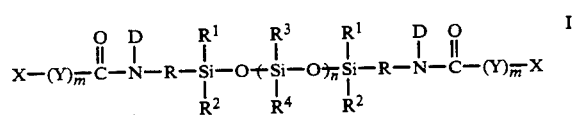

wherein:
X are monovalent moieties having ethylenic unsaturation which can be the same or different;
Y are divalent linking groups which can be the same or different;
m is an integer of 0 to 1;
D are monovalent moieties which can be the same or different selected from the group consisting of hydrogen, an alkyl group of 1 to about 10 carbon atoms, aryl, and substituted aryl;
R are divalent hydrocarbon groups which can be the same or different;
R$^1$ are monovalent moieties which can be the same or different selected from the group consisting of alkyl, substituted alkyl, aryl, and substituted aryl;
R$^2$ are monovalent moieties which can be the same or different selected from the group consisting of alkyl, substituted alkyl, aryl, and substituted aryl;
R$^3$ are monovalent moieties which can be the same or different selected from the group consisting of alkyl, substituted alkyl, vinyl, aryl, and substituted aryl;
R$^4$ are monovalent moieties which can be the same or different selected from the group consisting of alkyl, substituted alkyl, vinyl, aryl, and substituted aryl; and
n is an integer of about 270 to about 1000.

A composition which is curable to a pressure sensitive adhesive comprising the above polymer and a sufficient amount of tackifier. Thhe invention also relates to fluorosilane compounds useful in the preparation of silicone macromonomer, their preparation and the preparation of silicone macromonomer.

30 Claims, No Drawings

RADIATION-CURABLE SILICONE ELASTOMERS AND PRESSURE SENSITIVE ADHESIVES

This is a continuation of application Ser. No. 07/411,410, filed Sept. 22, 1989, now abandoned.

FIELD OF THE INVENTION

This application relates to silicone elastomers and silicone pressure sensitive adhesives (PSAs) and to compositions for producing the same. This application also relates to silicone PSA-coated sheet materials, to fluorosilane compounds useful as terminating agents in anionic siloxane polymerizations and their preparation, and to a method of preparing siloxane macromolecular monomer.

BACKGROUND OF THE INVENTION

Silicone elastomers and pressure sensitive adhesives (PSAs) are known for their chemical inertness and resistance to weathering. Other characteristics include retention of elastomeric character at low temperature, resistance to thermal degradation and retention of good mechanical properties at elevated temperature, a low dielectric constant, and excellent pressure sensitive adhesion to low energy surfaces. Thus, these materials are well-suited to demanding industrial applications and find wide use in the electrical and aerospace industries.

Silicone elastomers have traditionally been prepared by compounding gums of high molecular weight polyorganosiloxanes, filler, processing aids, and peroxide curing agents. The resulting composition is then cured at elevated temperature, i.e., from about 150° C. to about 250° C., depending upon the peroxide utilized. Drawbacks of such high temperature vulcanizable elastomers include the difficulty of processing or milling the high molecular weight gum and silica, the high temperature requirement, and, sometimes, the need for high pressure, as well. Silicone PSAs have been prepared similarly but with MQ tackifying resin substituted for the filler. However, there are several major disadvantages associated with this method of preparation of silicone PSAs. First of all, the mixture must be applied from solvent to improve its processability. This necessitates drying ovens and pollution abatement equipment, and it also places limitations on coating thickness due to the difficulty of rapidly removing solvent without generating bubbles or imperfections in thick films. Secondly, curing at an elevated temperature precludes the use of many substrate materials which do not possess sufficient heat stability. Finally, the cure may variably continue for days or weeks after the thermal treatment, leading to increased crosslink densities. This is a particularly troublesome problem for silicone PSAs which, upon aging, show decreased peel adhesion and tack properties. Room temperature vulcanizable (RTV) elastomers have been developed but have, in general, required lengthy cure times in order to obtain complete cure or have exhibited inferior properties. Thus, there has been a recognized need in the art (see, e.g., U.S. Pat. No. 4,675,346) for solventless silicone compositions with good processability that cure rapidly and completely at moderate temperatures to elastomers or PSAs possessing good and stable properties.

Workers in the art have looked upon radiation curing as a means of overcoming the above-mentioned disadvantages and have functionalized silicone gums in various ways to allow for cure with actinic radiation at moderate temperature. This has been successfully applied to low molecular weight gums (i.e., gums which cure to provide a low molecular weight between crosslinks) as disclosed in U.S. Pat. Nos. 4,369,300 (Carter et al.), 4,563,539 (Gornowicz et al.), and 4,605,712 (Mueller et al.) and by Yu et al. in J. Appl. Polym. Sci. 30, 2115 (1985). However, the materials resulting from the curing of these low molecular weight gums have a high crosslink density and therefore do not possess good elastomeric properties. Similar problems are observed in U.S. Pat. No. 4,370,358 (Hayes et al.) which describes an ultraviolet (UV) light curable silicone PSA derived from epoxy functional silicone polymer (chosen from a range of molecular weights) in admixture with MQ silicone resin and a cationic photoinitiator. Although acceptable peel adhesion values are shown immediately after curing for the lower molecular weight PSAs, a large drop in peel values occurs upon aging at room temperature. This is indicative of the continued curing which is a typical problem with cationic systems. The low peel values ultimately obtained reflect a high crosslink density (low molecular weight between crosslinks) and less than optimum elastomeric character. U.S. Pat. No. 4,777,276 (Rasmussen et al.) also concerns low molecular weight materials, disclosing acrylamido- and methacrylamido-acyl oligomers which are the acrylamido-acyl and methacrylamido-acyl derivatives of amino-, hydroxyl-, and thiol-substituted polyoxyalkylene, polyalkyleneimine, polyester, polyolefin, polyacrylate, polyamide, polymerized fatty acids, and polysiloxane oligomers having at least one hydroxyl, thiol, or primary or secondary amino group and a molecular weight of about 200 to about 20,000.

It has long been known (Lewis, *Rubb. Chem. Tech.* 35, 1222 [1962]) that to obtain good elastomeric properties in a traditional peroxide-cured silicone rubber that there should be between about 200 and about 600 monomer units, i.e., a molecular weight of from about 15,000 to about 45,000, between crosslinks. Accordingly, efforts have been made to increase the molecular weight between the functional sites which lead to crosslinks in the radiation curable silicone systems. The problem has been that, as the molecular weight between reactive functional sites is increased, the concentration of reactive functionality is diluted, giving systems in which rapid and complete cure is difficult, if not impossible, to achieve. This is illustrated in U.S. Pat. No. 4,640,940 (Jacobine et al.) which gives examples which show that, as the molecular weight of a (meth)acrylate-terminated polydimethylsiloxane is increased from 1,700 to 5,000 to 12,000 to 28,000, the required cure time greatly increases and the degree of cure (measured as Durometer Shore A hardness) falls off. U.S. Pat. No. 4,675,346 (Lin et al.) discloses UV curable silicone compositions containing linear silicone resin (of at least about 150 siloxane units) having terminal acrylic groups, at least about 10% of a reinforcing fumed silica filler, and a photoinitiator. This reference states that, as molecular weight increases, the decreasing acrylic function density increases the difficulty of UV cure until the composition becomes uncurable with silicones above about 50,000 molecular weight. These systems are further described in U.S. Pat. Nos. 4,575,545 (Nakos et al.) and 4,575,546 (Klemarczyk et al.) as being in general difficult, if at all possible, to cure with chemical free radical generators at ambient temperatures, due to the low acrylic functionality density of the resins. Materials "having as a central feature a characteristic of having at least two terminal acrylate unsaturations and an organosilicone containing backbone" are also described in European Patent Publication No. 170219, published Feb. 5, 1986 (Dentsply).

One approach to improving curability has been to increase the density of reactive functionality by placing multiple reactive groups on a given siloxane unit. Silicone compositions reflecting this approach are disclosed in U.S. Pat. Nos. 4,503,208 (Lin et al.) and 4,640,940 (Jacobine et al.), as well as in U.S. Pat. Nos. 4,293,397 (Sato et al.), 4,364,809 (Sato et al.), 4,591,608 (Okinoshima), and 4,603,086 (Fujii et al.). The use of multiple groups improves cure rate to some extent over the use of "monofunctional" materials, yet the reported curing rates are still longer than desired for an industrially viable process.

U.S. Pat. Nos. 4,575,545 (Nakos et al.) and 4,575,546 (Klemarczyk et al.) attempt to extend the molecular weight range of UV curable silicone polymers by preparing block polymers consisting of acrylate-rich and acrylate-poor regions. However, these materials are difficult to prepare, and the relatively highly cross-linked acrylate-rich segments may be detrimental to the elastomeric properties of the cured silicone rubber.

It is therefore an object of this invention to provide silicone compositions which, even at high molecular weight, may be rapidly, completely, and reliably radiation cured.

It is also an object of this invention to provide radiation-cured silicone elastomers having properties which are equal to or better than those of prior art radiation-cured silicone elastomers.

It is another object of this invention to provide radiation-cured silicone PSAs having stable properties.

It is yet another object of this invention to provide silicone PSAs having improved tack properties and silicone elastomers having controlled mechanical properties.

It has been discovered that these and other objects and advantages which will become apparent from the following discussion may be achieved via the use of polysiloxanes having terminal groups which, in addition to being reactive, are also capable of intermolecular hydrogen bonding.

SUMMARY OF THE INVENTION

This invention provides silicone compositions which cure rapidly, completely, and reliably upon exposure to radiation to give silicone elastomers and PSAs possessing good and, in some cases, improved properties which are stable and controllable. Organopolysiloxanes have been chemically tailored to contain terminal functionality which provides rapid and complete cure even at high molecular weight, thereby overcoming the molecular weight limitations of prior art radiation-cured systems. Thus, an important feature of this invention is the use of terminal groups which not only contain ethylenic unsaturation (so as to be free-radically polymerizable) but which, in addition, possess both hydrogen bond donor and acceptor capabilities. The use of such groups enables rapid and complete cure, such that prior art problems with stability of properties are also overcome, and renders achievable the uniform cure of thick films. Such groups additionally enable careful regulation of crosslink density, providing control over elastomeric and PSA properties which has heretofore not been achievable. Other advantages of the silicone compositions of this invention include ease of preparation, ease of processing (which reduces or even eliminates the need for solvent), and, as radiation-curable systems, the ability to cure without damage to heat-sensitive substrates.

More specifically, this invention provides a silicone composition which is radiation curable to an elastomer comprising an organopolysiloxane polymer or a mixture of organopolysiloxane polymers having the following general formula:

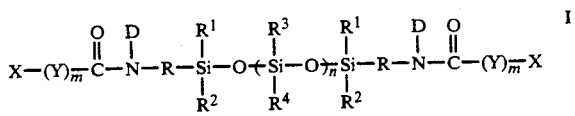

wherein:
X is a group having ethylenic unsaturation;
Y is a divalent linking group;
m is an integer of 0 to 1;
D is selected from the group consisting of hydrogen, an alkyl group of 1 to about 10 carbon atoms, aryl, and substituted aryl;
R is a divalent hydrocarbon group;
$R^1$ are monovalent moieties which can be the same or different selected from the group consisting of alkyl, substituted alkyl, aryl, and substituted aryl;
$R^2$ are monovalent moieties which can be the same or different selected from the group consisting of alkyl, substituted alkyl, aryl, and substituted aryl;
$R^3$ are monovalent moieties which can be the same or different selected from the group consisting of alkyl, substituted alkyl, vinyl, aryl, and substituted aryl; and
$R^4$ are monovalent moieties which can be the same or different selected from the group consisting of alkyl, substituted alkyl, vinyl, aryl, and substituted aryl; and
n is an integer of about 270 to about 1000.

The invention also provides a composition which is curable to a pressure sensitive adhesive (PSA) comprising the above composition and sufficient tackifier to endow the cured composition with adhesive tack at the use temperature.

The silicone composition curable to an elastomer and the silicone composition curable to a PSA of the invention can additionally comprise a low molecular weight organopolysiloxane polymer or a mixture of low molecular weight organopolysiloxane polymers according to the formula

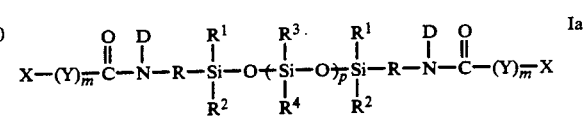

wherein:
p is an integer of about 35 to about 270; and
X, Y, m, D, R, $R^1$, $R^2$, $R^3$ and $R^4$ are as defined above, monofunctional siloxane macromolecular monomer, i.e., macromonomer, represented by Formula IX below, or a combination of the two. The compositions can further comprise an amount of free radical initiator sufficient to initiate polymerization of the composition, and they can also contain filler.

Cured versions of the compositions and PSA-coated sheet materials are provided, as are novel monoaminoalkyl-terminated organopolysiloxane and a method for its preparation, novel fluorosilane compounds useful as terminating agents in anionic siloxane polymerizations, and methods of macromonomer and fluorosilane compound preparation, as described below.

DETAILED DESCRIPTION OF THE INVENTION

The silicone composition of the invention is represented by Formula I. An example of a preferred organopolysiloxane comprises the organopolysiloxane of Formula I wherein X comprises

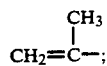

Y comprises

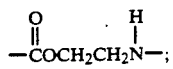

$m-1$; $D=H$; R comprises $-CH_2CH_2CH_2-$; and $R^1$, $R^2$, $R^3$ and $R^4$ each comprise $-CH_3$.

Another preferred organopolysiloxane comprises the organopolysiloxane of Formula I wherein X comprises $CH_2=CH-$; Y comprises

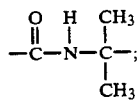

$m=1$, $D=H$, R comprises $-CH_2CH_2CH_2-$; and $R^1$, $R^2$, $R^3$ and $R^4$ each comprise $-CH_3$.

Another preferred organopolysiloxane comprises the organopolysiloxane of Formula I wherein X comprises $CH_2=CH-$; $m=0$, $D=H$, R comprises $-CH_2CH_2CH_2-$; and $R^1$, $R^2$, $R^3$ and $R^4$ each comprise $-CH_3$.

The silicone compositions of this invention comprise terminally difunctional, i.e., telechelic, silicones represented by Formula I above, which can be prepared by reaction of an organopolysiloxane diamine, represented by the general formula

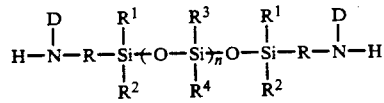

II where n, R, $R^1$, $R^2$, $R^3$, $R^4$, and D are as defined above, with an electrophile having ethylenic unsaturation, X, and such other functionality that, upon reaction with the organopolysiloxane diamine, not only a terminal X group but also an amide, urea, or urethane moiety is provided. Examples of the types of functionality required in such electrophilic compounds include acid halide, acid anhydride, and cyclic anhydride (such as the azlactone ring), each of which provides an amide moiety upon reaction with the diamine, and isocyanate, which provides a urea moiety.

Preferably, X comprises

wherein $R^5$ is selected from the group consisting of hydrogen and $-COOH$ and $R^6$ is selected from the group consisting of hydrogen, methyl, and $-CH_2COOH$. Most preferably, $R^5$ comprises hydrogen and $R^6$ is selected from the group consisting of hydrogen and methyl. The reaction can be carried out at temperature of about $-10°$ C. to about 50° C. and under atmospheric pressure by combining the diamine and the electrophile while providing appropriate mixing. A nonreactive organic solvent can be used as a diluent but is not necessary, and the two reactants can be charged into the reaction vessel in any order. Alternatively, an organopolysiloxane diamine according to Formula II above can be reacted first with a compound containing two electrophilic groups, e.g., a diisocyanate, (or with a compound such as phosgene) and the resultant product reacted in a second step with a nucleophile, e.g., an amine or an alcohol, to provide terminally difunctional silicone according to Formula I. When an alcohol such as hydroxyethyl acrylate, hydroxyethyl methacrylate, or hydroxypropyl methacrylate is utilized, the product organopolysiloxane contains urethane moieties.

Organopolysiloxane diamines useful in the preparation of the telechelic silicones of this invention can be prepared in various ways. In a first method, an organopolysiloxane terminated at both chain ends with hydroxy groups, as represented by the general formula

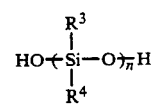

III where $R^3$, $R^4$, and n are as defined above, can be subjected to a condensation reaction with a compound represented by the general formula

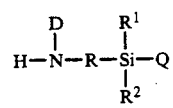

IV where D, R, $R^1$, and $R^2$ are as defined above and Q is a hydroxy group or a hydrolyzable group. A second method involves the reaction of a cyclic organosiloxane, represented by the general formula

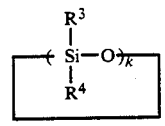

V where $R^3$ and $R^4$ are as defined above and k is a positive integer of 3 to 8, with an amine functional endblocker, represented by the general formula

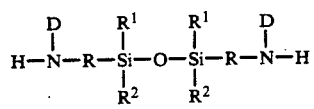

VI where D, R, $R^1$, and $R^2$ are as defined above, in the presence of a basic catalyst such as tetramethylammonium hydroxide or triorganosilanolate. A third method, a modification of the second, is preferred and involves running the reaction in two stages utilizing a minimum amount of an essentially anhydrous amino alkyl functional silanolate catalyst represented by the general formula

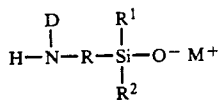

(VII)

where D, R, $R^1$, and $R^2$ are as defined above and $M^+$ is a cation selected from the group consisting of $K^+$, $Na^+$, and tetraorganoammonium ion, with $N(CH_3)_4^+$ being preferred. In the first stage of the reaction, a low molecular weight organopolysiloxane diamine, represented by the general formula

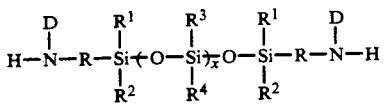

(VIII)

where D, R, $R^1$, $R^2$, $R^3$, and $R^4$ are as defined above and x is an integer of about 4 to about 40, is prepared by reacting an amine functional disiloxane endblocker represented by Formula VI above with a cyclic organosiloxane represented by Formula V in the presence of a catalytic amount of essentially anhydrous amino alkyl functional silanolate represented by Formula VII in an inert atmosphere such as nitrogen or argon. The preferred catalyst for use in this reaction is 3-aminopropyl dimethyl tetramethylammonium silanolate, which can be obtained as a crystalline solid from the reaction of one molar equivalent of 1,3-bis(3-aminopropyl) tetramethyldisiloxane with two molar equivalents of tetramethylammonium hydroxide pentahydrate in tetrahydrofuran under reflux, followed by drying under vacuum for five hours (0.1 mm) at 60° C. The amount of catalyst employed should be less than about 0.05 percent, preferably about 0.005 to about 0.03 percent, by weight of the resultant organopolysiloxane diamine. The reaction can be carried out in bulk at a temperature of 80°–90° C., and under these conditions is usually complete in about 0.5–2 hours, as judged by substantially complete disappearance of the endblocker of the reaction mixture as determined by vapor phase chromatography. The second stage of the reaction involves the slow addition of the remainder of the cyclic organosiloxane required to achieve the desired molecular weight. This addition is preferably carried out dropwise at such a rate that the cyclic organosiloxane is incorporated into the polymer about as fast as it is added, usually in about five to seven hours at the reaction temperature of 80°–90° C. By utilizing this two-stage method with a minimum amount of essentially anhydrous catalyst, organopolysiloxane diamines represented by Formula II above can be consistently prepared having excellent difunctionality with little contamination from monofunctional and nonfunctional polysiloxane impurities.

Preferred organopolysiloxane diamines for use in preparing the telechelic silicones of this invention are those for which n is an integer of about 300 to about 700, R is selected from the group consisting of alkylene of one to about twelve carbon atoms, alkylarylene, and arylene, $R^1$ and $R^2$ are independently selected from the group consisting of alkyl of one to about twelve carbon atoms, substituted alkyl of one to about twelve carbon atoms, aryl, and substituted aryl, $R^3$ and $R^4$ are at least 50% methyl with the remainder selected from the group consisting of alkyl of two to about twelve carbon atoms, substituted alkyl of two to about twelve carbon atoms, vinyl, aryl, and substituted aryl, and D is hydrogen. Such a range of molecular weights provides the best balance of properties in the PSA compositions. Most preferably, R is alkylene of one to about twelve carbon atoms and $R^1$, $R^2$, $R^3$, and $R^4$ are methyl, as polydimethylsiloxanes are the most readily available, the most inert, and provide the greatest adhesion to low energy surfaces.

Examples of electrophiles suitable for reaction with organopolysiloxane diamines to produce the telechelic silicones of the invention include but are not limited to isocyanatoethyl methacrylate, alkenyl azlactones such as vinyl dimethyl azlactone and isopropenyl dimethyl azlactone, m-isopropenyl-α, α-dimethyl benzyl isocyanate, and acryloyl ethyl carbonic anhydride. Some electrophiles, e.g., isocyanatoethyl methacrylate, are commercially available, and others can be prepared via literature methods. Alkenyl azlactones and their preparation are described in U.S. Pat. No. 4,777,276 (Rasmussen et al.), the disclosure of which is incorporated herein by reference. Acryloyl ethyl carbonic anhydride can be prepared from ethyl chloroformate and acrylic acid by the method of R. Hatada and H. Kondo given in *Bull. Chem. Soc. Japan.* 41 (10), 2521(1968), the disclosure of which is also incorporated herein by reference. Preferred electrophiles include those selected from the group consisting of isocyanatoethyl methacrylate, vinyl dimethyl azlactone, and acryloyl ethyl carbonic anhydride.

The silicone compositions of the invention can, depending upon their viscosity, be coated, extruded, or poured, and rapidly, completely, and reliably radiation cured to elastomers (even at high molecular weight) by exposure to electron beam, visible, or ultraviolet radiation. Curing should be carried out in as oxygen-free an environment as possible, e.g., in an inert atmosphere such as nitrogen gas or by utilizing a barrier of radiation-transparent material having low oxygen permeability. Curing can also be carried out under an inerting fluid such as water. When visible or ultraviolet radiation is used for curing, the silicone compositions also contain photoinitiator. Suitable photoinitiators include benzoin ethers, benzophenone and derivatives thereof, acetophenone derivatives, camphorquinone, and the like. Photoinitiator is generally used at a concentration of from about 0.1% to about 5% by weight of the total polymerizable composition, and, if curing is carried out under an inerting fluid, the fluid is preferably saturated with the photoinitiator or photoinitiators being utilized in order to avoid the leaching of initiator from the silicone composition. The rapid cure observed for these materials allows for the use of very low levels of photoinitiator relative to the prior art, hence uniform cure of thick sections can be achieved due to deeper penetration of radiation. If desired, the silicone compositions of the invention can also be cured thermally, requiring the use of thermal initiator such as peroxides, azo compounds, or persulfates generally at a concentration of from about 1% to about 5% by weight of the total polymerizable composition. It is preferable that any initiator (thermal or photo-) utilized be soluble in the silicone compositions themselves, requiring no use of solvent. Liquid initiators are especially preferred.

The radiation-curable silicone pressure sensitive adhesive compositions of the invention can be prepared by mixing one or more of the telechelic silicones represented by Formula I above with a sufficient amount of a tackifier, preferably a silicone MQ tackifying resin, to impart to the cured composition a degree of adhesive tack at the use temperature, e.g., from about 80 to about 150 parts by weight resin to 100 parts by weight silicone at room temperature. Such resins are known in the art, as referenced in U.S. Pat. No. 4,370,358, and are commercially available as approximately 50 to 60 weight percent solutions in solvents such as toluene or xylene. The telechelic silicones can be added to the MQ resin solution to provide a high solids, e.g., a 60-80 weight percent solids, composition which can be coated on a substrate, cured by exposure to radiation (as described above), and then dried to effect solvent removal. Alternatively, the drying step can precede the curing step, or the solvent can be stripped after the MQ resin solution and telechelic silicone are combined, in this case providing a 100% solids composition which can then be coated or extruded and then cured. Curing of the silicone PSA compositions can be effected via application of either radiation or heat utilizing appropriate initiators, as described above, with the MQ resin solvent aiding in initiator dissolution. Curing of the PSAs prior to drying, i.e., in a swollen state, is preferred since better tack and peel adhesion properties are obtained via this method. The silicone elastomer compositions of the invention, i.e., silicone compositions containing no MQ resin, may also be cured in a swollen state via addition of solvent, if a "soft", i.e., compliant, elastomer after drying is desired for a particular application. By varying the degree of swelling, controlled variation of PSA properties and elastomeric properties can be achieved.

Nonpolar solvents such as cyclohexane, heptane, toluene, hexamethyldisiloxane, and cyclic siloxanes such as hexamethylcyclotrisiloxane ($D_3$), octamethylcyclotetrasiloxane ($D_4$), and decamethylcyclopentasiloxane ($D_5$); or mixtures thereof are especially useful as diluents for curing in a swollen state. The silicone compositions are readily soluble in them, they do not interfere with the curing reaction since they are nonreactive under the conditions of the free radical reaction and are transparent to the radiant energies used for cure, and they do not significantly solvate apart aggregates of the polar end groups of the silicone compositions which, although we do not wish to be bound by any theory, we believe may be the reasons for the rapid, reliable, and complete cure of the compositions of this invention.

In addition to the technique of curing in a swollen state, controlled variation of properties can be achieved by including low molecular weight difunctional organopolysiloxane, as described above, or monofunctional siloxane macromolecular monomer, i.e., silicone macromonomer, or both in the silicone elastomer or PSA compositions.

Desired properties can be obtained via variation in the nature, molecular weight, and amount of the material added. Low molecular weight difunctional silicone can be prepared by the methods described above and, when blended with higher molecular weight difunctional silicone (using a polar solvent such as tetrahydrofuran, if necessary, to compatibilize the two) and then copolymerized, serves to modify the properties of the polymerized composition so as to provide elastomers with improved tensile strength or PSAs with reduced peel adhesion and reduced tack.

Preferably the amount of low molecular weight difunctional silicone does not exceed 90 weight percent of the composition in the case of the elastomers and 80 weight percent of the composition in the case of the PSAs. If the concentration of low molecular weight difunctional organopolysiloxane is too high, the materials resulting from curing of these compositions have a high crosslink density (low molecular weight between crosslinks) and do not possess good elastomeric properties in the case of the elastomers, and lack sufficient compliance to give good tack and peel adhesion performance in the case of the PSAs. Copolymerization of silicone macromonomer, represented by Formula IX below, wherein q is an integer of 0 to 1, s is an integer of 1-3, r is an integer of about 35 to about 700, $R^7$ are monovalent moieties which can be the same or different selected from the group consisting of alkyl, substituted alkyl, alkoxy, alkylamino, hydroxyl, aryl, and substituted aryl, and X, Y, m, D, R, $R^2$, $R^3$, and $R^4$ are as defined above, yields PSAs with increased tack, i.e., improved "finger appeal", or elastomers with increased compliance.

Preferably the amount of silicone macromonomer does not exceed about 90 weight percent of the composition in the case of the elastomers and about 80 weight percent of the composition in the case of the PSAs. If the concentration of silicone macromonomer is too high, the materials resulting from curing of these compositions have a low crosslink density (incomplete network formation) resulting in elastomers which have relatively low tensile strength, and PSAs which have poor shear strength. Low molecular weight difunctional organopolysiloxane can be used in combination with silicone macromonomer to controllably vary the properties of the materials resulting from curing of these compositions. In this case preferably the high molecular weight difunctional polyorganosiloxane of the invention comprises at least about 10 weight percent of the composition, with the low molecular weight difunctional polyorganosiloxane and the silicone macromonomer independently comprising up to about 90 weight percent of the composition. Materials resulting from the curing of compositions included in this preferred region have the best elastomeric performance (tensile and elongation) for the elastomers and the best PSA performance (tack, shear strength, and peel adhesion) for the PSAs.

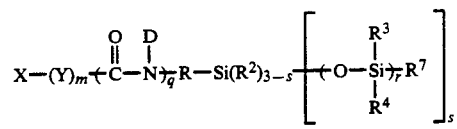

IX

Silicone macromonomer for which q is zero, which does not contain the above-shown amido group, e.g., methacryloxypropyl-terminated polydimethylsiloxane, can be utilized but is not preferred due to lower copolymerizability. Silicone macromonomer can be prepared by anionic polymerization as described in U.S. Pat. No. 4,728,571 (Clemens et al.), the disclosure of which is incorporated herein by reference. This "traditional" method of preparation involves the use of functionalized chlorosilanes to terminate the anionic polymerization. Such chlorosilane terminating agents are extremely sensitive to moisture and, during storage or transfer, hydrolysis to a difunctional disiloxane can occur. The presence of this type of impurity in silicone macromonomer can then lead to excessive crosslinking in subsequent free radical polymerizations, resulting in loss of compliance. It has been discovered, however, that functionalized fluorosilanes can be prepared and that such fluorosilanes can be effectively utilized as terminating agents for the preparation of silicone macromonomer. Since the fluorosilanes are quite hydrolytically stable under neutral or acidic conditions, this macromonomer preparative method is preferred. Fluorosilane terminating agents according to the following general formula $$X-(Y)_m-(C(=O)-N)_q-R-Si(R^2)_{3-s}F_s \quad X$$

wherein:
X is a monovalent moiety having ethylenic unsaturation;
Y is a divalent linking group;
m is an integer of 0 to 1;
D is a monovalent moiety selected from the group consisting of hydrogen, an alkyl group of 1 to about 10 carbon atoms, aryl, and substituted aryl;
q is an integer of 0 to 1;
R is a divalent hydrocarbon group;
$R^2$ is a monovalent moiety selected from the group consisting of alkyl, substituted alkyl, aryl, and substituted aryl;
s is an integer 1 to 3;
are useful as the above described terminating agents.

Novel compounds of the above formula comprise those wherein the following is true:
when q=0 and m=1, R comprises $C_3$-$C_{12}$ alkylene group and $R^2$ comprises methyl;
when q=0 and m=0, R comprises an alkylene group.
Compounds of the formula $$X-(Y)_m-(C(=O)-N)_q-R-Si(R^2)_{3-s}F_s \quad X$$

wherein:
X is a monovalent moiety having ethylenic unsaturation;
Y is a divalent linking group;
m is an integer of 0 to 1;
D is a monovalent moiety selected from the group consisting of hydrogen, an alkyl group of 1 to about 10 carbon atoms, aryl, and substituted aryl;
q is an integer of 0 to 1;
R is a divalent hydrocarbon group;
$R^2$ is a monovalent moiety selected group consisting of alkyl, substituted alkyl, aryl, and substituted aryl; and
s is an integer 1 to 3, can be prepared by combining a silane selected from the group consisting of halogen-substituted silanes, nitrogen-substituted silanes, and oxygen-substituted silanes with a suitable nonreactive solvent, such as isopropyl alcohol, 2-butanone, or tetrahydrofuran, in order to form a solution. The use of water-miscible solvents, optionally in combination with other non-reactive solvents, such as hydrocarbon solvents, aids in homogenizing the acidic fluoride reagent with the silane starting material, resulting in rapid and complete conversion to product. The solution thus formed is treated by combining it with at least about a molar equivalent, preferably at least about a 5 percent molar excess of an acidic fluoride reactant, such as hydrofluoric acid, potassium bifluoride, ammonium fluoride, or the like, in order to form a solution of the compound of Formula X. Preferably the solution is then diluted at least about twofold with water, followed by extraction of said solution with a water insoluble organic solvent. Suitable water insoluble organic solvents include ethyl acetate, methylene chloride, diethyl ether, and the like. The extract is then evaporated to obtain the compound of Formula X. This method provides essentially quantitative yields of the fluorosilanes, which can then be purified by conventional methods, e.g., by distillation or recrystallization. Some of the above-mentioned substituted silanes are commercially available, e.g., methacryloxypropyl dimethyl chlorosilane, methacryloxypropyl trimethoxy silane, and bis(methacryloxypropyl) tetramethyl disiloxane. Others can be easily prepared, e.g., via reaction of bis(aminopropyl) tetramethyl disiloxane with an electrophile such as isocyanatoethyl methacrylate or vinyl dimethyl azlactone. The fluorosilane terminating agents can be used to prepare silicone macromonomer according to Formula IX above by adding the terminating agent, preferably at least about a molar equivalent of the terminating agent, to a solution of a living polymeric siloxanolate in a suitable non-hydroxylic solvent, such as tetrahydrofuran, preferably at a temperature of from about 25° to about 100° C., as described in Clemens et al. Purification of the macromonomer can then be effected by precipitation in methanol.

A preferred fluorosilane terminating agent comprises the fluorosilane terminating agent of the Formula X, wherein
X comprises $$CH_2=C(CH_3)-;$$

Y comprises $$-C(=O)-O-;$$

q=0; m=1; s=1; R comprises $-CH_2CH_2CH_2-$; and $R^2$ comprises $-CH_3$.

Another preferred fluorosilane terminating agent comprises the fluorosilane terminating agent of the Formula X, wherein
X comprises $$CH_2=CH-;$$

m=1;
Y comprises $$-C(=O)-N(H)-C(CH_3)(CH_3)-;$$

q=1; D=H; R comprises $-CH_2CH_2CH_2-$; s=1; and
$R^2$ comprises $-CH_3$.

Another preferred fluorosilane terminating agent comprises the fluorosilane terminating agent of the Formula X, wherein
X comprises

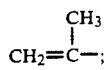

m = 1;
Y comprises

q = 1; D = H; R comprises —CH$_2$CH$_2$CH$_2$—;
R$^2$ comprises —CH$_3$; and
s = 1.

Amine-substituted fluorosilane terminating agents, represented by Formula XI wherein D, R, and s are as defined above, can also be used.

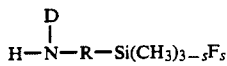     XI

Compounds of the formula

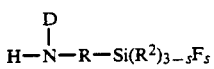     XIA wherein D, R, R$^2$, and s are as defined above are prepared by a somewhat different procedure which first involves combining an oxygen-substituted silane and a suitable solvent, such as cyclohexane, toluene, benzene, chloroform, and the like in order to form a solution. The use of such water-immiscible solvents allows for continuous azeotropic removal and separation of the water formed in the reaction. The solution thus formed is reacted by combining it with at least about a molar equivalent, preferably at least about a 5 percent molar excess of an acidic fluoride reactant, such as hydrofluoric acid, potassium bifluoride, ammonium fluoride, or the like, preferably ammonium fluoride, with azeotropic removal of water generated. This provides the amine hydrofluoride substituted fluorosilane which can then be converted to the free amine by heating it in a suitable solvent with about a 1 percent molar excess to about a 5 percent molar excess of a compound selected from the group consisting of monosubstituted or disubstituted lower alkylamino silanes and hexamethyl disilazane, preferably hexamethyl disilazane. The monosubstituted or disubstituted lower alkylamino silane can thus contain one or two lower alkyl groups. Preferably each lower alkyl group independently comprises one to about four carbon atoms. The amine-substituted fluorosilane can be isolated by evaporation of the solvent and distillation of the product under reduced pressure.

An example of a preferred fluorosilane terminating agent comprises the fluorosilane terminating agent of the Formula XI, wherein D = H; R comprises —CH$_2$CH$_2$CH$_2$—; and s = 1.

This preferred terminating agent is prepared by combining 1,3-bis(aminopropyl)tetramethyldisiloxane and a hydrocarbon solvent having a boiling point ranging from about 75° C. to about 85° C. in order to form a solution. Suitable hydrocarbon solvents include cyclohexane, benzene, heptane, and the like. The solution thus formed is reacted by combining the solution with at least about a molar equivalent of an acidic fluoride reactant, preferably at least about a 5 percent molar excess of an acidic fluoride reactant, such as hydrofluoric acid, potassium bifluoride, ammonium fluoride, or the like, preferably ammonium fluoride, with azeotropic removal of water. This provides the amine hydrofluoride substituted fluorosilane isolated as the crystalline hydrofluoride salt precipitate, which can then be converted to the free amine by heating a slurry of the salt in a water-immiscible solvent boiling in the range of about 35°-50° C., e.g., methylene chloride, with about a 1 percent molar excess to about a 5 percent molar excess of a compound selected from the group consisting of monosubstituted or disubstituted lower alkylamino silanes and hexamethyl disilazane. The amine-substituted fluorosilane can be separated from the solvent by evaporation of the solvent and distillation of the product under reduced pressure.

The resultant amine-substituted fluorosilane products should be stored in closed containers protected from atmospheric moisture and can be used to prepare novel monoaminoalkyl-terminated organopolysiloxane according to Formula XII below, wherein D, R, R$^2$, s, R$^3$, R$^4$, and R$^7$ are as defined above, and r is an integer of about 5 to about 1000,

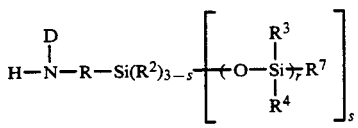     XII by adding the fluorosilane terminating agent, preferably at least about a molar equivalent of fluorosilane terminating agent, to a solution of a living polymeric siloxanolate in a suitable non-hydroxylic solvent, such as tetrahydrofuran, preferably at a temperature ranging from about 25° to about 100° C., as described in Clemens et al. Silicone macromonomer according to Formula IX above, useful in the silicone elastomer and PSA compositions of this invention, can be prepared by reaction of the monoaminoalkyl-terminated organopolysiloxane of Formula XII with an electrophile as described above, e.g., isocyanatoethyl methacrylate or vinyl dimethyl azlactone.

The silicone compositions of the invention curable to elastomers can be frothed using an inert gas such as nitrogen, to make a foam and can contain an amount of silica filler sufficient to provide the level of reinforcement necessary for a particular application, e.g., up to about 50 percent by weight of the total composition. The silicone PSA compositions of the invention can also contain silica filler for modification of PSA properties, e.g., at levels up to about 10-15 percent by weight of the total composition. Either hydrophilic or hydrophobic silica can be utilized, but hydrophobic silica is preferred due to its reduced tendency to "structure", i.e., to hydrogen bond with the polysiloxane and form an elastic mass prior to cure. Such structuring can impede normal processing operations such as molding and extrusion (See the discussion of fillers in "Silicone Elastomers", *Encyclopedia of Polymer Science and Engineering*, 1989, Volume 15, 271-308). Other common non-copolymerizable additives such as pigments, dyes, quartz powder, glass fibers, calcium carbonate, flame retardants, thermal stabilizers, polymerization inhibitors, plasticizers, adhesion promoters, and the like can also be included.

The silicone compositions of this invention, depending upon their viscosity, can be coated via any of a variety of conventional coating methods, such as roll coating, knife coating, or curtain coating, or can be extruded. The silicone PSA compositions can be applied to at least a portion of at least one major surface of a suitable flexible or inflexible backing materials and cured to produce PSA-coated sheet materials. Useful flexible backing materials include paper, plastic films such as poly(propylene), poly(ethylene), poly(vinyl chloride), poly(tetrafluoroethylene), polyester [e.g., poly(ethylene terephthalate)], polyimide film such as DuPont's Kapton TM, cellulose acetate, and ethyl cellulose. Backings can also be of woven fabric formed of threads of synthetic or natural materials such as cotton, nylon, rayon, glass, or ceramic material, or they can be of nonwoven fabric such as air-laid webs of natural or synthetic fibers or blends of these. In addition, suitable backings can be formed of metal, metallized polymeric film, or ceramic sheet material. The PSA-coated sheet materials can take the form of any article conventionally known to be utilized with PSA compositions, such as labels, tapes, transfer tapes (comprising a film of the PSA borne on at least one release liner), signs, covers, marking indices, and the like. Primers can be utilized, but they are not always necessary.

EXAMPLES

All parts and percentages in the examples are by weight unless otherwise specified.

Test Methods

The test methods used to evaluate the elastomers and PSA-coated flexible sheet materials of the examples are industry standard tests. The standard tests are described in various publications of the American Society for Testing and Materials (ASTM), Philadelphia, Pa., and the Pressure Sensitive Tape Council (PSTC), Glenview, Ill., and are detailed below. The reference source of each of the standard test methods is also given.

Viscosity Measurements

The bulk viscosity of functional polysiloxanes was determined by using Brookfield Viscometer Model RVTDV-II with programmable temperature controller. 15 g of liquid polymer was poured into the chamber and placed in the thermostat. The measurement was taken after thermal equilibrium was reached. Spindles #21 or 27 were used depending on the viscosity of the sample. The data is included in Table 1.

Mechanical Properties

Mechanical testing was performed on an Instron Model 1122 tensile tester. Testing was performed according to a modification of ASTM D412-83. Samples were prepared according to Method B (cut ring specimens). Type 1 rings (5.1 cm circumference) were produced with a specially-designed precision ring cutter. The Instron analog output signal was routed to a digital voltmeter with accuracy better than 0.5 percent, and the digital readings were recorded by a computer. Modifications to the ASTM were as follows:
1. The crosshead speed was 12.7 cm/min rather than 50.8 cm/min.
2. The test fixture shafts (upper and lower jaw) both rotated at 30 RPM in the same direction in order to maintain uniform strain throughout the entire ring.
3. The thickness of the rings was 0.5 mm.

Shear Strength

Reference: ASTM: D3654-78; PSTC-7

The shear strength is a measure of the cohesiveness or internal strength of an adhesive. It is based upon the amount of force required to pull an adhesive strip from a standard flat surface in a direction parallel to the surface to which it has been affixed with a definite pressure. It is measured in terms of the time (in minutes) required to pull a standard area of adhesive coated sheet material from a stainless steel test panel under stress of a constant, standard load.

The tests were conducted on adhesive-coated strips applied to a stainless steel panel such that a 12.7 mm by 12.7 mm portion of each strip was in firm contact with the panel with one end portion of the tape being free. The panel with coated strip attached was held in a rack such that the panel formed an angle of 178° with the extended tape free end which was then tensioned by application of a force of one kilogram applied as a hanging weight from the free end of the coated strip. The 2° less than 180° was used to negate any peel forces, thus insuring that only the shear forces were measured, in an attempt to more accurately determine the holding power of the tape being tested. The time elapsed for each tape example to separate from the test panel was recorded as the shear strength. Unless otherwise noted, all shear failures reported herein were cohesive failures of the adhesive.

Peel Adhesion

Reference: ASTM D3330-78 PSTC-1 (11/75)

Peel adhesion is the force required to remove a coated flexible sheet material from a test panel measured at a specific angle and rate of removal. In the examples, this force is expressed in Newtons per decimeter (N/dm) width of coated sheet. The procedure followed was:
1. A 12.7 mm width of the coated sheet was applied to the horizontal surface of a clean glass test plate with at least 12.7 lineal cm in firm contact. A 2 kg hard rubber roller was used to apply the strip.
2. The free end of the coated strip was doubled back nearly touching itself so the angle of removal was 180°. The free end was attached to the adhesion tester scale.
3. The glass test plate was clamped in the jaws of a tensile testing machine which was capable of moving the plate away from the scale at a constant rate of 2.3 meters per minute.
4. The scale reading in Newtons was recorded as the tape was peeled from the glass surface. The data is reported as the average of the range of numbers observed during the test.

Tack

Reference: ASTM D2979-71

Pressure sensitive tack is a measure of the ability to form a bond with the surface of another material upon brief contact under light pressure. In the examples, this ability was measured using a Polyken Probe Tack Tester as the force in grams required to separate a standard ½ cm diameter stainless steel probe from an adhesive-coated flexible sheet at a rate of separation of 1 cm/sec after contacting the adhesive for 1 sec at a pressure of 100 g/cm². Reported values are the average of 10 readings.

Abbreviations:

PDMS—polydimethylsiloxane
MAUS—methacryloxyurea siloxane
ACMAS—acrylamidoamido siloxane
MACMAS—methacrylamidoamido siloxane
MeStUS—α-methylstyrylurea siloxane
ACMS—acrylamido siloxane
IEM—isocyanatoethyl methacrylate
VDM—vinyl dimethyl azlactone
IDM—isopropenyl dimethyl azlactone
m-TMI—m-isopropenyl-α,α-dimethyl benzyl isocyanate
GMA—glycidyl methacrylate Examples 1a–1c Difunctional polysiloxanes terminated on both ends with ethylenically unsaturated groups were prepared as described below. They are identified in the foregoing description and in the tables as 1a–1c (MAUS), 2a–2c (ACMAS), 3a–3c (MACMAS), 4a–4c (ACMS), 5a–5c (MeStUS). Synthesis of difunctional precursors for all free-radically polymerizable siloxanes described in this application was performed in the following way: a 500 mL 3-necked round bottom flask equipped with thermometer, mechanical stirrer, dropping funnel and dry argon inlet was charged with 3.72 g bis(3-aminopropyl) tetramethyldisiloxane and 18 g of octamethylcyclotetrasiloxane ($D_4$) which had been previously purged for 10 minutes with argon. The flask contents were heated to 80° C. with an oil bath, and a trace (about 0.03 to 0.05 g) of catalyst—anhydrous 3-aminopropyl dimethyl tetramethylammonium silanolate—was added via a spatula. The reaction was stirred at 80° C. and after 30 minutes of stirring had become quite viscous. Vapor phase chromatography (VPC) showed that the endblocker had completely disappeared. To the resultant reaction mixture (which consisted of a 1,500 molecular weight polysiloxane with aminopropyl endgroups, cyclic siloxanes and active catalyst) was added dropwise over a six hour period 330 g of argon-purged $D_4$, resulting in a further rise in the viscosity. Heating the reaction flask contents at 80° C. was continued overnight. The catalyst was decomposed by heating at 150° C. for ½ hour, and the product was stripped at 140° C. at 0.1 mm pressure until no more volatiles distilled (ca. 1½ hour), resulting in 310 g of a clear, colorless, viscous oil (a yield of 88% of theoretical). The molecular weight of the product determined by acid titration was 21,200. Using this procedure, but varying the ratio of endblocker to $D_4$, silicone diamines with molecular weights of 35,000 and 55,000 were prepared. A 10,000 molecular weight silicone diamine was also prepared by this procedure as a comparative example.

Polydimethylsiloxane terminated on both ends with methacryloxyurea groups and having an average molecular weight of about 21,000 was prepared by thoroughly mixing 200 g (0.01 mole) of aminopropyl-terminated polydimethylsiloxane prepared according to the above description with 3.1 g (0.02 mole) of isocyanatoethyl methacrylate (IEM), commercially available from Showa Rhodia, at room temperature. The viscosity of the reaction mixture increased as the reaction progressed. The number average molecular weight of the difunctional polysiloxane was determined by acid titration of the precursor and was confirmed by gel permeation chromatography (GPC) analysis before and after capping with IEM. The polysiloxanes of Examples 1b and 1c were prepared analogously by using aminopropyl-terminated polydimethylsiloxane precursors with molecular weights of 35,000 and 55,000, respectively.

Examples 2a–2c, 3a–3c, 4a–4c, 5a–5b

Other free-radically polymerizable siloxanes of the present invention were prepared by reacting aminopropyl-terminated polydimethylsiloxanes prepared as in Example 1 with other capping agents, such as vinyl dimethyl azlactone (VDM) and isopropenyl dimethyl azlactone (IDM), prepared as described in U.S. Pat. No. 4,777,276 (Rasmussen et al.), or with m-isopropenyl-α,α-dimethyl benzyl isocyanate available from Cyanamid under the tradename m-TMI ™, at room temperature to form a series of polysiloxanes with acrylamidoamido (ACMAS, Examples 2a–2c), methacrylamidoamido (MACMAS, Examples 3a–3c), and α-methylstyryl urea (MeStUS, Examples 4a–4c) groups on both ends, respectively. 21,000 MW acrylamido functional siloxane (ACMS, Example 5a) was prepared by adding a solution of 0.80 g (5.5 mmol) acryloyl ethyl carbonic anhydride (prepared from ethyl chloroformate and acrylic acid according to the method of R. Hatada and H. Kondo, *Bull. Chem. Soc. Japan*, 41(10),2521 (1968)) in 5 mL $CH_2Cl_2$ to 50.4 g (2.5 mmol) 21,000 MW degassed aminopropyl-terminated polydimethylsiloxane in a 100 mL round bottom flask, stirring 30 minutes at room temperature under nitrogen, and distilling off solvent on a rotary evaporator. 35,000 MW ACMS (Example 5b) was prepared similarly. The chemical type of the end groups, the number average molecular weight (rounded to the nearest thousand), and the Brookfield viscosity at 35° C. of the polymers described in Examples 1a–5b are given in Table 1.

TABLE 1

| Example | Functional Group | $(M_n)$ | Viscosity at 35° C. (Pa·s × 10³) |
|---------|------------------|---------|----------------------------------|
| 1a | MAUS | 21,000 | 13,000 |
| 1b |  | 35,000 | 31,800 |
| 1c |  | 55,000 |  |
| 2a | ACMAS | 21,000 | 49,600 |
| 2b |  | 35,000 | 56,000 |
| 2c |  | 55,000 |  |
| 3a | MACMAS | 21,000 | 2,940 |
| 3b |  | 35,000 | 7,940 |
| 3c |  | 55,000 |  |
| 4a | MeStUS | 21,000 | 42,000 |
| 4b |  | 35,000 | 71,200 |
| 4c |  | 55,000 |  |
| 5a | ACMS | 21,000 | 1,990 |
| 5b |  | 35,000 | 6,460 |

Example 6

Preparation of Aminoalkyl Fluorosilane Terminating Agent

A 500 mL, 3 neck round bottom flask was charged with 49.6 g 1,3-bis(3-aminopropyl)tetramethyldisiloxane, 29.6 g ammonium fluoride, and 300 mL cyclohexane. While heating under reflux, water was removed by means of a Dean-Stark trap. After 18 hours, 4.4 mL of water had been collected, and the clear, colorless solution was transferred while warm to a 500 mL 1-neck round bottom flask. The solvent was distilled on a rotary evaporator to provide 165 grams of white solid.

This was dissolved in 200 mL of methylene chloride, 30 g of hexamethyldisilazane was added, and the mixture was stirred and heated under reflux for 5 hours. The flask was fitted for distillation and the solvent removed under aspirator vacuum. The product was distilled (boiling point of 70° C.) at aspirator vacuum to provide 3-aminopropyldimethyl fluorosilane as a clear, colorless oil. The yield was 54 g (100%), which was determined to be pure by vapor phase chromatography. The structure was confirmed by NMR spectroscopy.

Example 7

Preparation of Trifluorosilane Terminating Agent

A solution of 22.1 g 3-aminopropyltriethoxysilane in 75 mL dry tetrahydrofuran in a 500 mL polypropylene beaker was cooled to 0°-5° C., and 13.9 g 2-vinyl-5,5-dimethyl azlactone was added dropwise slowly with stirring. The reaction mixture was stirred for 15 minutes, and 75 mL of isopropyl alcohol was added, followed by the slow addition of 16 g 48% aqueous hydrofluoric acid. The mixture was stirred for 15 minutes at 0° C. and then diluted with 200 mL $H_2O$. The product was extracted with methylene chloride, the extracts dried using $MgSO_4$, and the solvent removed with a rotary evaporator. The product, N-(3-trifluorosilyl-propyl)-2-acrylamido-2,2-dimethyl acetamide was obtained as a thick oil (23 g). The structure was confirmed by NMR.

Example 8

Preparation of Methacryloxyureapropyldimethyl Fluorosilane Terminating Agent

A solution of 49.7 g 1,3-bis(3-aminopropyl) tetramethyldisiloxane in 55 mL of dry tetrahydrofuran in a polypropylene beaker was cooled to 0°-5° C., and 55.6g isocyanatoethyl methacrylate was added dropwise slowly with stirring. The reaction mixture was stirred for 1 hour, and 100 mL of isopropyl alcohol and 0.12 g of the inhibitor, 2,5-di-tert butylhydroquinone, were added, followed by the slow addition of 32 g 48% aqueous hydrofluoric acid. The mixture was stirred for 60 minutes at 0° C., refrigerated overnight, and then diluted with 200 mL $H_2O$. The product was extracted with methylene chloride, the extract dried using $MgSO_4$, additional inhibitor was added and the solvent removed with a rotary evaporator. The product was obtained as white crystalline material. The structure was confirmed by NMR.

Example 9

Preparation of Methacryloxypropyldimethyl Fluorosilane Terminating Agent

Into a 250 mL 3-necked round bottom flask equipped with a dry ice condensor, addition funnel, magnetic stirring bar, and thermometer with attached temperature monitor was charged 65.3 mg methylene blue, 31.2 g (0.33 mol) freshly distilled dimethylchlorosilane (available from Huls America), and 50 mL cyclohexane. The resulting mixture was heated to 45° C. with a heat lamp and held there while a mixture of 38.6 mg 15% Pt° in divinyltetramethyldisiloxane (prepared according to methods described in U.S. Pat. No. 3,775,452), 37.8 g (0.30 mol) allyl methacrylate (available from Alcolac under the tradename Sipomer TM AM), and 25 mL cyclohexane was Charged dropwise over 30 minutes. Within 15 minutes of completing the addition the reaction exothermed to 70° C. The temperature was moderated to 50° C. by external cooling with a water bath and within an hour had dropped back to 45° C. At this point, analysis by capillary gas chromatography showed 98% conversion of the allyl methacrylate to hydrosilation product (3-methacryloxypropyldimethylsilyl chloride and its hydrolysis products). The mixture was cooled in an ice-water bath to 0° to 5° C., and 25 mL isopropanol was charged dropwise over 5 minutes. The resulting solution was transferred to a polypropylene beaker, and 25.7 g (0.62 mol) 48% aqueous HF was added portionwise over 5 minutes while still cooling in an ice-water bath. The resulting mixture was stirred for 50 minutes, at which point capillary gas chromotography showed complete reaction. After dilution with 30 mL water and 25 mL cyclohexane, the mixture was transferred to a separatory funnel, the bottom aqueous layer discarded, and the organic layer washed two times with 30 mL water. t-Butylhydroquinone (73.5 mg) was added to the resulting organic layer which was then dried over magnesium sulfate. After filtration and washing the cake with 30 mL cyclohexane, 68.0 mg of phenothiazine was added, and the solvents were stripped on a rotary evaporator at aspirator vacuum and 32° C. The product was simple distilled under reduced pressure (bp 65°-70° C. at 0.5 mm Hg) to yield 45.0 g (0.22 mol, 73% yield) product after a 1.2 g allyl methacrylate-containing forecut.

Example 10

Preparation of Aminopropyl-terminated Polydimethylsiloxane n-Butyl lithium (10 mL, 2.5 M) was added to 7.4 g octamethylcyclotetrasiloxane ($D_4$) under argon to form lithium silanolate initiator. After stirring for 30 minutes, a solution of 250 g hexamethylcyclotrisiloxane ($D_3$) in 250 g dry tetrahydrofuran was added and the reaction stirred at room temperature for 18 hours. To the resulting viscous syrup was added 3.4 g 3-aminopropyldimethyl fluorosilane terminating agent. The viscosity rapidly decreased. After stirring for 2 hours, the solvent was distilled off on a rotary evaporator. The product was filtered to remove lithium fluoride and provided 250 g of silicone monoamine as a clear, colorless oil. Titration with 0.1 N HCl gave a number average molecular weight, $\overline{M}_n$, of 9400 (theoretical $\overline{M}_n = 10,000$).

Example 11

Preparation of Acrylamidoamido-functional Tri-branched Polydimethylsiloxane Macromonomer Polydimethylsiloxane with MW 10,000 was prepared by polymerizing $D_3$ using n-butyl lithium as an initiator and was reacted at room temperature with trifluorosilane terminating agent, prepared as described in Example 7, to obtain 3-arm branched siloxane macromonomer. A colorless, viscous oil was obtained after purification, as described in Example 10.

Examples 12a–12c

Unfilled silicone elastomer film was made by UV-irradiation of MAUS liquid rubber in the presence of photoinitiator. 10 g liquid rubber as in Ex.1a (21K MAUS) and 0.02 g (0.2 wt %) 2-hydroxy-2-methyl-1-phenylpropan-1-one, available from EM Industries, Inc. under the trade name Darocur TM 1173 were mixed. The mixture was degassed and knife coated between two polyester films to provide a coating thickness of 0.5 mm. The sample was exposed to UV irradiation at 2.6 mW/cm² (Sylvania Blacklight) for 5 minutes on each side, and the silicone rubber film was removed from between the liners. Similarly silicone rubbers were made of MAUS liquid rubbers of Ex. 1b (Ex.12b) and of Ex.1c (Ex.12c) using the same weight fraction of Darocur ™ 1173 The mechanical properties as determined by Instron testing are shown in Table 2.

Examples 13a–13c

Unfilled silicone elastomers were made by UV curing of ACMAS liquid rubbers with different molecular weights prepared as in Examples 2a–2c, using the procedure as outlined in Examples 12a–12c. Test results of the mechanical properties are shown in Table 2.

Examples 14a–14c

Unfilled silicone elastomers were made by UV curing of MACMAS liquid rubbers with different molecular weights prepared as in Examples 3a–3c, using the procedure as outlined in Examples 12a–12c. Test results of the mechanical properties are given in Table 2.

Examples 15a–15b

Unfilled silicone elastomers were made by UV curing of ACMS liquid rubbers of different molecular weights, prepared as in Examples 5a–5b, using the procedure outlined in Examples 12a–12c. Test results of the mechanical properties are given in Table 2.

Example C16 (Comparative)

Free-radically polymerizable siloxanes were prepared following the teachings of U.S. Pat. No. 4,293,397 to compare the curability of glycidyl methacrylate (GMA) capped silicone diamines with the free-radically polymerizable siloxanes disclosed in the present invention at the same molecular weight and derived from the same diamine. Utilizing the procedure described in Example 4 of U.S. Pat. No. 4,293,397, 40.34 g (2 mmol) degassed 20,171 MW amine terminated PDMS synthesized as described in Example 1 above was placed in a 250-mL 2-neck flask containing 1.47 g (10.3 mmol) glycidyl methacrylate and 9.4 mg methoxyhydroquinone. An overhead stirrer and a nitrogen inlet were attached, the headspace was flushed with nitrogen, and the reaction mixture was stirred for 65 hours at 60° C. A portion of the resulting clear viscous GMA capped liquid rubber was mixed with 0.2 wt % Darocur ™ 1173 and cured by exposure to UV-lights as in Ex.12a–12c. The mechanical properties of the film were tested and are included in Table 2 for comparison. The mechanical properties of silicone rubbers of the present invention, Ex. 12, 13, 14 and 15 are better than those of the comparative example, C16, in terms of stress at break and modulus, indicating poor curability of GMA-functionalized liquid rubber.

TABLE 2

| Example | Type | $\overline{MW}_{mr,1}$ ($\overline{M}_n$) | Modulus (MPa) | Stress at break (MPa) | Strain at break (%) |
|---|---|---|---|---|---|
| 12a | MAUS | 21000 | 0.759 | 1.103 | 172 |
| 12b | | 35000 | 0.455 | 1.379 | 297 |
| 12c | | 55000 | 0.386 | 1.683 | 433 |
| 13a | ACMAS | 21000 | 0.765 | 1.952 | 257 |
| 13b | | 35000 | 0.448 | 2.076 | 365 |
| 13c | | 55000 | 0.572 | 2.110 | 482 |
| 14a | MACMAS | 21000 | 0.765 | 1.000 | 174 |
| 14b | | 35000 | 0.538 | 0.862 | 308 |
| 14c | | 55000 | 0.621 | 1.910 | 493 |
| 15a | ACMS | 21000 | 0.407 | 1.103 | 225 |
| 15b | | 35000 | 0.317 | 1.262 | 355 |
| C16 | GMA capped | 20000 | 0.117 | 0.303 | 249 |

Example C17 (Comparative)

Free-radically polymerizable siloxanes were prepared following the teachings of U.S. Pat. No. 4,603,086 to compare the curability of 1,6-hexanediol diacrylate (HDDA) capped silicone diamines with the free-radically polymerizable siloxanes disclosed in the present invention at the same molecular weight and derived from the same diamine. Utilizing the procedure described in Example 1 of U.S. Pat. No. 4,603,086, 1.99 g (8.8 mmol) HDDA in 4 mL toluene was placed in a 250-mL 3 neck round bottom flask equipped with an addition funnel, nitrogen inlet, and overhead stirrer. After flushing the headspace with nitrogen, the contents were heated to 70° C., and 40.34 g (2 mmol) of degassed 20,171 MW amine-terminated PDMS synthesized according to Example 1 above was added dropwise to the stirred solution over the course of an hour. After the addition was complete, the temperature was raised to 80° C. for 30 minutes, then the toluene was distilled off on a rotary evaporator. A portion of the resulting clear viscous oil was mixed with 0.2 wt % Darocur ™ 1173, coated between two polyester films, and exposed to low intensity UV lights for 10 minutes as in Example 12a. The sample gelled but did not give a coherent film, indicating poorer curability when compared with the liquid silicone rubbers of the present invention.

Examples 18a and 18b

These examples demonstrate that silicone elastomers with modified properties (modulus, elongation at break, tensile at break) can be made by the UV curing of liquid rubbers "swollen" with solvent. 10 g of 21,000 MW MAUS liquid rubber was dissolved in 10 g cyclohexane (50% swollen) 0.04 g Darocur ™ 1173 (2-hydroxy-2-methyl-1-phenylpropan-1-one) was added, and the sample was cured by exposure to UV lights as in Example 12a. The resulting elastomeric film was dried in vacuo, and its properties were measured using an Instron tensile tester. Similarly, a sample was prepared containing 30 wt % 21,000 MW MAUS and 70 wt % cyclohexane. The coated and cured film was dried in vacuo, and its mechanical properties measured using an Instron tensile tester. The data is included in Table 3.

These results demonstrate that elastomers with lower modulus, i.e., more compliant than the control sample of Example 13a, can be prepared by curing in a swollen state.

TABLE 3

| Example | Type | Cured | Modulus (MPa) | Stress at break (MPa) | Strain at break (%) |
|---|---|---|---|---|---|
| 13a | 21000 MW MAUS | neat | 0.765 | 1.952 | 257 |
| 18a | 21000 MW MAUS | 50% swollen | 0.379 | 0.434 | 177 |
| 18b | 21000 MW | 70% | 0.207 | 0.296 | 281 |

TABLE 3-continued

| Example | Type | Cured | Modulus (MPa) | Stress at break (MPa) | Strain at break (%) |
|---|---|---|---|---|---|
| | MAUS | swollen | | | |

Examples 19a and 19b

These examples demonstrate another means of modification of the mechanical characteristics of silicone elastomers by co-curing difunctional free-radically curable polysiloxanes with silicone macromonomers (monofunctional) to give networks containing dangling ends. Aminopropyl-terminated polydimethylsiloxane of 13,000 MW was prepared according to the method of Example 10 and was then further functionalized to introduce a free-radically polymerizable group by reaction with vinyl dimethyl azlactone at room temperature according to the procedure described in Example 1 for difunctional polysiloxanes to obtain 13,000 MW ACMAS macromonomer (ACMASmac). 21,000 MW ACMAS (8 g) and 13,000 MW ACMASmac (2 g) (80/20 w/w) were mixed with 0.02 g Darocur TM 1173, coated between two polyester films, and cured as described in Example 12a. Similarly, a film was made containing 50 wt % 21,000 MW ACMAS and 50 wt % 13,000 MW ACMASmac. The mechanical properties (Instron) of these films were compared with the properties of the reference (21,000 MW ACMAS film), as shown in Table 4. Softer elastomers with a tailored modulus can be prepared by including silicone macromonomer in the silicone elastomer compositions of the present invention.

Examples 20a and 20b

Similarly, samples were prepared by mixing 21,000 MW ACMAS and branched silicone macromonomer made as described in Example 11. 21,000 MW ACMAS was mixed with 30,000 (3×10,000) MW branched ACMASmac at two different weight ratios, 80/20 and 50/50. 0.2 wt % Darocur TM 1173 was added to each, and the samples were coated between two polyester films and cured as described in Example 12a. The mechanical properties (Instron) of the cured samples were compared with the properties of the reference (21,000 MW ACMAS film). As in Examples 19a and 19b, a decrease in modulus resulted from introduction of siloxane macromonomer into the network, which demonstrates that such a method can be applied to modify the mechanical characteristics of silicone elastomers.

TABLE 4

| Example | Type | Ratio | Modulus (MPa) | Stress at break (MPa) | Strain at break (%) |
|---|---|---|---|---|---|
| 13a | 21K ACMAS | 100/0 | 0.765 | 1.952 | 257 |
| 19a | 21K ACMAS/ 13K ACMASmac | 80/20 | 0.621 | 1.552 | 259 |
| 19b | 21K ACMAS/ 13K ACMASmac | 50/50 | 0.345 | 0.965 | 263 |
| 20a | 21K ACMAS/ 3 × 10K ACMASmac | 80/20 | 0.441 | 1.496 | 274 |
| 20b | 21K ACMAS/ 3 × 10K ACMASmac | 50/50 | 0.179 | 0.800 | 314 |

Example 21

This example illustrates the effect of curing time on the mechanical characteristics of a slowly curing system. A mixture of 21,000 MW MAUS (10 g) and 21,000 MW MeStUS (10 g) and 0.04 g Darocur TM 1173 was coated and cured by exposure to UV lights for 10 minutes as in Example 12a. Another sample of the same formulation was exposed to UV for a total of 30 minutes, 15 minutes on each side. Mechanical properties were measured using an Instron tensile tester, and are given below. The sample which was cured for 30 minutes had properties similar to the fast curing 21,000 MW MAUS. The slower cure rate observed in this case is apparently due to the fact that α-methylstyryl groups are not able to homopolymerize. This example illustrates that poor mechanical characteristics of elastomers derived from functional siloxanes of the same molecular weight but different functionalities can be considered as a measure of incomplete crosslinking.

| 21K MAUS/ 21K MeStUS 50/50 | Cure time (min) | Modulus (MPa) | Stress at break (MPa) | Strain at break (%) |
|---|---|---|---|---|
| | 10 | 0.290 | 1.234 | 313 |
| | 30 | 0.531 | 1.483 | 280 |

Examples 22a–22e

These examples demonstrate that by blending low molecular weight liquid rubbers with the high molecular weight rubbers of the invention, one can tailor the mechanical properties of the elastomers made therefrom. 10,000 MW ACMAS liquid silicone rubber was prepared analogously to high molecular weight liquid rubbers by the method described in Example 1. 35,000 MW (i.e., 35K) ACMAS (9.5 g) was mixed with 10K ACMAS (0.5 g) (95/5 w/w, Example 22a) and 0.02 g Darocur TM 1173 and was coated and cured into an elastomeric film. Similarly, formulations containing b: 90/10, c: 80/20, d: 65/35, e: 50/50 weight ratios of 35K ACMAS/10K ACMAS were prepared and cured. The mechanical properties of each of the samples were tested using an Instron tensile tester, and the data is given in Table 5. The test results for elastomer made of 35K ACMAS (Example 13b) are included as a reference. Elastomer made of pure 10K ACMAS was tested as a comparative example, and this data is also included in the table. The data indicates that the mechanical properties of radiation-curable silicone elastomers can be tailored within a broad range by co-curing high molecular weight liquid rubbers of the present invention with lower molecular weight components.

TABLE 5

| Example | Type | Ratio | Modulus (MPa) | Stress at break (MPa) | Strain at break (%) |
|---|---|---|---|---|---|
| 13b | ACMAS 35K/10K | 100/0 | 0.448 | 2.076 | 365 |
| 22a | ACMAS 35K/10K | 95/5 | 0.607 | 2.114 | 340 |
| 22b | ACMAS 35K/10K | 90/10 | 0.662 | 2.552 | 328 |
| 22c | ACMAS 35K/10K | 80/20 | 0.641 | 2.634 | 300 |
| 22d | ACMAS 35K/10K | 65/35 | 0.800 | 3.662 | 277 |
| 22e | ACMAS 35K/10K | 50/50 | 0.841 | 3.979 | 255 |

TABLE 5-continued

| Example | Type | Ratio | Modulus (MPa) | Stress at break (MPa) | Strain at break (%) |
|---|---|---|---|---|---|
| Comparative example | ACMAS 10K | | 1.324 | 2.021 | 153 |

Examples 22f–22h

These examples demonstrate that elastomers with tailored properties can be made by the method of the invention of the formulations comprising high and low MW liquid silicon rubbers and silicon macromonomer. The formulation as in Example 22e (35K ACMAS/10K ACMAS (50/50)) was mixed with silicone macromonomer prepared as in Examples 19a–19b (13K ACMASmac) in weight ratios: f: 80/20, g: 65/35, h: 50/50 and cured after adding 0.2 weight percent of Darocur ™ 1173. The mechanical properties of each of the samples were tested using Instron tensile tester and the data is given in Table 5a. The test results for elastomer made of the mixture of 35K ACMAS/10K ACMAS (50/50 weight ratio) (Example 22e) are included as references.

TABLE 5a

| Example | Type | Ratio | Modulus (MPa) | Stress at break (MPa) | Strain at break (%) |
|---|---|---|---|---|---|
| 22e | 35K/10K ACMAS/ 13K ACMASmac | 100/0 | 0.841 | 3.979 | 255 |
| 22f | 35K/10K ACMAS/ 13K ACMASmac | 80/20 | 0.379 | 1.745 | 238 |
| 22g | 35K/10K ACMAS/ 13K ACMASmac | 65/35 | 0.273 | 1.097 | 229 |
| 22h | 35K/10K ACMAS/ 13K ACMASmac | 50/50 | 0.183 | 0.614 | 215 |

Example 23

This example demonstrates that free-radical cure of the liquid rubbers can be accomplished by using a thermal initiator at elevated temperatures. 55K MAUS (10 g) was mixed with 0.1 g (1 wt %) t-amyl peroxypivalate available from Pennwalt under the trade name Lupersol ™ 554M75, coated between two polyester films, and cured at 65° C. for 1 hour. The mechanical characteristics of the elastomer were checked and compared with elastomer made of 55K MAUS liquid rubber by UV curing (Example 12c).

| 55K MAUS | Modulus (MPa) | Stress at break MPa | Strain at break (%) |
|---|---|---|---|
| UV cured (Ex. 12c) | 0.386 | 1.683 | 433 |
| heat cured | 0.469 | 2.076 | 437 |

Examples 24a–24e

These examples illustrate that elastomers with good mechanical performance (better than RTV silicone elastomers and comparable, or better, than standard peroxide cured silicone elastomers) can be made by formulating liquid rubbers with reinforcing filler and curing. Without trying to optimize the performance, the effect of the content of the reinforcing filler on mechanical properties has been studied on a few samples. 18 g 20K MAUS liquid rubber was thoroughly mixed with 2 g (10 wt %) of hydrophobic fumed silica available from Wacker Chemie as HDK ™ H-2000 and Darocur ™ 1173 (0.2 wt %) and coated between two polyester films at a thickness of 0.5 mm. The sandwich was exposed to UV lights as in Example 12a for 5 minutes on each side. Similarly, mixtures with increasing viscosities were prepared containing 20 wt %, 30 wt % and 40 wt % silica. The mixtures were all cured to silicone elastomers having the mechanical properties shown in Table 6. Analogously, a silicone elastomer sample was prepared from 55K MAUS and 40 wt % silica, and the results of mechanical property testing for this sample are also included in Table 6.

TABLE 6

| Example | Type | Silica (wt %) | Modulus (MPa) | Stress at break (MPa) | Strain at break (%) |
|---|---|---|---|---|---|
| 24a | 21K MAUS | 10 | 0.937 | 1.710 | 169 |
| 24b | | 20 | 1.041 | 3.483 | 227 |
| 24c | | 30 | 1.386 | 4.621 | 246 |
| 24d | | 40 | 2.779 | 6.931 | 170 |
| 24e | 55K MAUS | 40 | 1.772 | 7.503 | 497 |

SILICONE PSAS

Example 25

5 g of 20K ACMAS was added to 8.3 g of a 60% solids solution of MQ resin in toluene (available from GE Silicones as catalog #SR 545) to yield a 75% solids solution. 0.1 g of Darocur ™ 1173 photoinitiator was added and, after shaking, the homogeneous solution was knife coated at 50 micrometers thick onto a 37 micrometer thick primed polyester film with an unprimed polyester film overleaf. This laminate was cured under low intensity UV lights for five minutes total as described above for the elastomers, the unprimed polyester stripped, and the resulting tape dried 10 minutes at 65° C. After conditioning overnight at constant temperature (22° C.) and humidity (50% RH), the tape tests described above were performed. Testing was repeated after one month of natural aging to investigate the stability of tape properties with time. Results are shown in Table 7.

Examples 26–32

Following the procedure of Example 25, PSAs with a 1/1 ratio of liquid rubber to MQ resin were prepared from liquid rubbers derived from different molecular weight diamines and functionalized with different capping agents. Results are shown in Table 7 and demonstrate that for a given molecular weight the MAUS, ACMAS, and ACMS liquid rubbers give comparable PSA performance on curing, that for a given functionality increasing molecular weight leads to higher peel adhesion and tack, and in all cases very little change in properties is observed on natural aging.

Examples 33–36

5 g of 35K ACMAS was formulated with 5.5, 8.3, 12.5, or 19.4 g 60% solids MQ resin in toluene and 0.1 g Darocur ™ 1173, coated, cured, dried, and tested following the procedure described in Example 25 above. Results are shown in Table 7 and demonstrate that highest peel adhesion is achieved at a 1/1.5 gum to resin ratio, while highest tack is achieved at a 1/1 gum to resin ratio for these formulations.

Examples 37-40

10K ACMAS was progressively substituted for 50K ACMAS in a 1/1 gum to resin formulation prepared, cured, dried, and tested according to the procedure given for Example 25. Results presented in Table 8 show that the low molecular weight material reduces peel and tack at high loadings.

Examples 41 and 42

Mixtures of 35K ACMAS and 35K MeStUS were formulated 1/1 with MQ resin and coated, cured, dried, and tested as described in Example 25 above. Results are shown in Table 8, demonstrating higher tack and peel adhesion at higher MeStUS loadings.

Examples 43-45

6.6 g of a 75% solids 1/1 35K ACMAS/MQ resin mixture containing 0.05g Darocur TM 1173 was diluted to either 60, 50, or 30% solids with 1.7, 3.4, or 10 g cyclohexane, coated, cured, dried, and tested as described in Example 25 above. Results shown in Table 9 demonstrate that curing in a swollen state enhances peel adhesion and tack performance without compromising shear adhesion.

Examples 46-48

13K VDM capped macromonomer (ACMASmac) was substituted for 20K ACMAS in a 1/1.2 gum to resin formulation, coated, cured, dried, and tested as described above in Example 25. Results in Table 10 show that the substitution of monofunctional silicone improved the tack without influencing peel adhesion.

Example 49

To 6.6 g of 75% solids 1/1 35K ACMAS/MQ resin in toluene was added 0.24 g (5 wt % based on overall solids) of hydrophobic fumed silica filler available from Wacker Chemie under the tradename HDK TM H2000 and 0.05 g (2 wt % based on gum) Darocur TM 1173 The resulting mixture was coated, cured, dried, and tested as described in Example 25 above. Results, presented in Table 11, show a reduced level of peel adhesion and tack relative to the same formulation without filler (Example 26).

Examples 50-52

A 75% solids solution of 1/1 35K ACMAS/MQ resin in toluene was knife coated at 50 micrometers thick onto a 37 micrometer thick primed polyester film with an unprimed polyester film overleaf. The resulting laminate was passed through an ESI Electrocurtain CB-150 electron beam processor and given doses of 2.5 (Example 50), 4.5 (Example 51), and 7.5 (Example 52) Mrad at 175 keV accelerating voltage. Drying and testing were done as described in Example 25, and the results, given in Table 11, demonstrate that good cure is obtained above about 2.5 Mrad as shown by the lack of cohesive failure in shear adhesion.

Example 53

This example demonstrates the use of a thermal initiator to cure a PSA formulation. To 5 g of 75% solids 1/1 35K ACMAS/MQ resin in toluene was added 0.56 g t-amyl peroxy pivalate available from Pennwalt under the tradename Lupersol TM 554M75 This solution was knife coated at 50 micrometers thick onto a 37 micrometer thick primed polyester film with an unprimed polyester film overleaf and the resulting laminate placed in a 65° C. oven for 30 min. The unprimed polyester was then stripped, and conditioning and testing were performed as described in Example 25 above with the results shown in Table 11.

Examples 54-56

These examples demonstrate curing of a PSA formulation with UV radiation from medium pressure mercury lamps. A mixture of 5 g 35K ACMAS, 8.3 g 60% solids MQ resin in toluene, and 0.1 g Darocur TM 1173 was prepared. A portion of this was coated with a knife coater 50 micrometers thick onto primed 37 micrometer polyester film, dried for 1 min in a 65° C. oven, then cured by passing open face through a PPG Industries UV Processor under nitrogen atmosphere two passes at 23 m per min with both lamps set at 80 watts/cm (200 watts/in) for a total dose of 200 mJ/cm$^2$. This (Example 54) was then conditioned and tested as described in Example 25 and shows that good performance is obtained even when curing is done in the absence of solvent. The same formulation was also cured in a swollen state with the medium pressure mercury lights by coating with an unprimed polyester overleaf as described in Example 25 above and leaving that in place while it was run through the processor two passes (Example 55) and 4 passes (Example 56) at 23 m per min, corresponding to 200, and 400 mJ/cm$^2$ doses. After stripping the overleaf, the samples were dried, conditioned, and tested as described in Example 25. Results presented in Table 11 show that curing with medium pressure UV gives comparable performance to curing with low intensity UV (Example 26).

Examples 57-61

These examples demonstrate the ability to vary the tack and peel adhesion performance of the cured PSA formulations by substitution of low molecular weight difunctional silicone or silicone macromonomer or both for the high molecular weight difunctional silicone in a 1/1.2 gum/MQ resin formulation. A mixture of 2.6 g 35K ACMAS, 1.4 g 10K ACMAS, 8 g 60% solids MQ resin in toluene, and 0 1 g Darocur TM 1173 was prepared. A portion of this was coated, cured, dried, and tested as described in Example 25 above. Results for this (Example 57) are shown in Table 11 along with results for Examples 58-61 which were prepared similarly but used the following materials for the gum portion of the PSA. Example 58: 2.6 g 35K ACMAS and 1.4 g 13K ACMASmac. Example 59: 2.4 g 35K ACMAS, 0.8 g 10K ACMAS, and 0.8 g 13K ACMASmac. Example 60: 1.6 g 35K ACMAS, 1.2 g 10K ACMAS, and 1.2 g 13K ACMASmac. Example 61: 1.2 g 35K ACMAS, 1 4 g 10K ACMAS, and 1.4 g 13K ACMASmac.

TABLE 7

| Example | Gum | Gum/Resin Ratio | Initial Peel (N/dm) | Tack (g) | Peel (N/dm) | Aged Shear* (min) | Tack (g) |
|---|---|---|---|---|---|---|---|
| 25 | 20K ACMAS | 1/1 | 42 | 399 | 42 | 600 po | 348 |
| 26 | 35K ACMAS | 1/1 | 53 | 544 | 50 | 565 po | 479 |
| 27 | 50K ACMAS | 1/1 | 59 | 640 | 59 | 10,000+ | 590 |
| 28 | 20K ACMS | 1/1 | 37 | 543 | 44 | 10,000+ | 467 |
| 29 | 35K ACMS | 1/1 | 48 | 563 | 46 | 10,000+ | 516 |
| 30 | 20K MAUS | 1/1 | 42 | 487 | 48 | 10,000+ | 413 |
| 31 | 35K MAUS | 1/1 | 59 | 683 | 55 | 7800 po | 581 |
| 32 | 50K MAUS | 1/1 | 72 | 764 | 70 | 7400 po | 667 |
| 33 | 35K ACMAS | 1/0.7 | 22 | 378 | 20 | 8400 po | 369 |
| 34 | 35K ACMAS | 1/1 | 55 | 611 | 48 | 8400 po | 522 |
| 35 | 35K ACMAS | 1/1.5 | 88 | 390 | 74 | 10,000+ | 85 |
| 36 | 35K ACMAS | 1/2.3 | 2 | 16 | 7 | 10,000+ | 0 |

*po = pop off (adhesive) failure

TABLE 8

| Example | Gum Mixture* | Peel (N/dm) | Initial Shear** (min) | Tack (g) | Aged Peel (N/dm) | Tack (g) |
|---|---|---|---|---|---|---|
| 37 | 90/10 50K ACMAS/ 10K ACMAS | 48 | 4600 po | 565 | 46 | 453 |
| 38 | 80/20 50K ACMAS/ 10K ACMAS | 55 | 2200 po | 559 | 48 | 359 |
| 39 | 65/35 50K ACMAS/ 10K ACMAS | 46 | 2900 po | 474 | 44 | 285 |
| 40 | 50/50 50K ACMAS/ 10K ACMAS | 39 | 2700 po | 365 | 35 | 240 |
| 41 | 80/20 35K ACMAS/ 35K MeSTUS | 59 | 50 po | 612 | 50 | 412 |
| 42 | 50/50 35K ACMAS/ 35K MeSTUS | 90 | 30 po | 730 | 48 | 537 |

*Gum to resin ratio held at 1/1 in all cases
**po = pop off (adhesive) failure

TABLE 9

| Example | % Solids During Cure | Peel (N/dm) | Initial Shear (min) | Probe Tack (g) |
|---|---|---|---|---|
| 43 | 60% | 57 | 8600 po | 533 |
| 44 | 50% | 61 | 10,000+ | 677 |
| 45 | 30% | 79 | 10,000+ | 718 |

TABLE 10

| Example | % Macromonomer | Peel (N/dm) | Initial Shear (min) | Probe Tack (g) |
|---|---|---|---|---|
| 46 | 0% | 59 | 10,000+ | 158 |
| 47 | 20% | 59 | 1276 | 189 |
| 48 | 50% | 55 | 486 | 231 |

TABLE 11

| Example | Peel (N/dm) | Initial Shear (min) | Probe Tack (g) |
|---|---|---|---|
| 49 | 39 | 10,000+ | 277 |
| 50 | 46 | 188 po | 534 |
| 51 | 53 | 70 po | 671 |
| 52 | 48 | 70 po | 760 |
| 53 | 44 | 370 po | 544 |
| 54 | 46 | 1800 po | 693 |
| 55 | 53 | 150 po | 598 |
| 56 | 57 | 1840 po | 657 |
| 57 | 51 | 10,000+ | 604 |
| 58 | 48 | 10,000+ | 702 |
| 59 | 40 | 10,000+ | 541 |
| 60 | 50 | 10,000+ | 422 |
| 61 | 47 | 10,000+ | 482 |

While this invention has been described in connection with specific embodiments, it should be understood that it is capable of further modification. The claims herein are intended to cover those variations which one skilled in the art would recognize as the chemical equivalent of what has been described here.

We claim:

1. A composition which is curable to an elastomer comprising:

a polymer or mixture of polymers of the formula

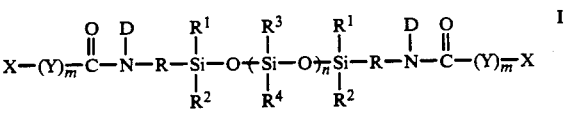

wherein:

X are monovalent moieties having ethylenic unsaturation which can be the same or different;

Y are divalent linking groups which can be the same or different;

m is an integer of 0 to 1;

D are monovalent moieties which can be the same or different selected from the group consisting of hydrogen, an alkyl group of 1 to about 10 carbon atoms, aryl, and substituted aryl;

R are divalent hydrocarbon groups which can be the same or different;

$R^1$ are monovalent moieties which can be the same or different selected from the group consisting of alkyl, substituted alkyl, aryl, and substituted aryl;

$R^2$ are monovalent moieties which can be the same or different selected from the group consisting of alkyl, substituted alkyl, aryl, and substituted aryl;

R³ are monovalent moieties which can be the same or different selected from the group consisting of alkyl, substituted alkyl, vinyl, aryl, and substituted aryl; and R⁴ are monovalent moieties which can be the same or different selected from the group consisting of alkyl, substituted alkyl, vinyl, aryl, and substituted aryl; and n is an integer of about 270 to about 1000.

2. A composition which is curable to a pressure sensitive adhesive comprising:
   (a) the composition of claim 1; and
   (b) sufficient tackifier to endow the cured composition with adhesive tack at the use temperature.

3. The composition of claim 2 wherein said tackifier comprises silicone MQ resin.

4. The composition of claim 1 which further comprises at least one of the additives selected from the group consisting of a filler, a nonpolar solvent, and a free radical initiator.

5. The composition of claim 2 which further comprises at least one of the following additives selected from the group consisting of a free radical initiator, a filler, and a nonpolar solvent.

6. An elastomer formed from the radiation curing of the composition of claim 1 or claim 4.

7. The elastomer formed from the radiation curing of the composition of claim 4, wherein said composition further comprises at least a nonpolar solvent and wherein said composition is cured in its swollen state.

8. A pressure sensitive adhesive formed from the radiation curing of the composition of claim 2, claim 3 or claim 5.

9. The pressure sensitive adhesive formed from the radiation curing of the composition of claim 5, which further comprises at least a nonpolar solvent and wherein said composition is cured in its swollen state.

10. The composition of claim 2 or 3 which comprises about 80 to about 150 parts by weight of tackifying resin per 100 parts by weight of polymer.

11. The composition of claim 1 or claim 4 which further comprises a polymer or mixture of polymers of the formula

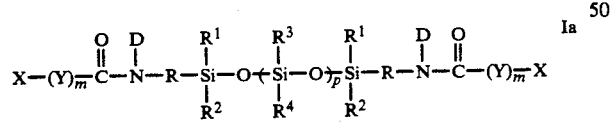

wherein:
p is an integer of about 35 to about 270;
X, Y, m, D, R, R¹, R², R³, and R⁴ are as defined in claim 1;
including sufficient polar solvent to compatibilize the polymers; and
wherein n is an integer of about 300 to about 700.

12. The composition of claim 11 wherein Ia comprises up to about 90 weight percent of the composition.

13. The composition of claim 1 or claim 4 which further comprises a silicone macromonomer or mixture of silicone macromonomers of the formula

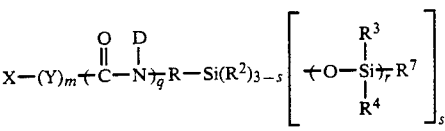

wherein
q is an integer of 0 to 1;
s is an integer of 1 to 3;
r is an integer of about 35 to about 700;
R⁷ are monovalent moieties which can be the same or different selected from the group consisting of alkyl, substituted alkyl, alkoxy, alkyl amino, hydroxyl, aryl, and substituted aryl; and
X, Y, m, D, R, R², R³, and R⁴ are as defined in claim 1.

14. The composition of claim 13 wherein said macromonomer or mixture of macromonomers comprises up to about 90 weight percent of the composition.

15. The composition of claim 2 or claim 5 which further comprises a polymer or mixture of polymers of the formula

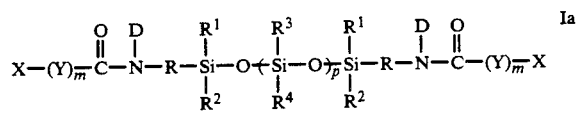

wherein:
p is an integer of about 35 to about 270; and
X, Y, m, D, R, R¹, R², R³, and R⁴ are as defined in claim 1;
including sufficient polar solvent to compatibilize the polymers.

16. The composition of claim 15 wherein said polymer or mixture of polymers comprises up to about 80 weight percent of the composition.

17. The composition of claim 2 or claim 5 which further comprises a silicone macromonomer or mixture of silicone macromonomers of the formula

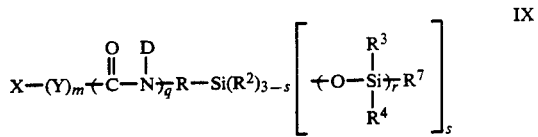

wherein:
q is an integer of 0 to 1;
s is an integer of 1 to 3;
r is an integer of about 35 to about 700;
R⁷ are monovalent moieties which can be the same or different selected from the group consisting of alkyl, substituted alkyl, alkoxy, alkyl amino, hydroxyl, aryl, and substituted aryl; and
X, Y, m, D, R, R², R³, and R⁴ are as defined in claim 1.

18. The composition of claim 17 wherein said macromonomer or mixture of macromonomers comprises up to about 80 weight percent of the composition.

19. A composition which is curable to an elastomer comprising:
   (a) a polymer or mixture of polymers of the formula

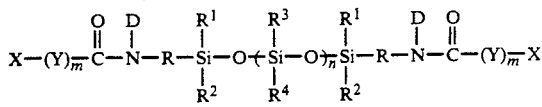

wherein
X are monovalent moieties having ethylenic unsaturation which can be the same or different;
Y are divalent linking groups which can be the same or different;
m is an integer of 0 to 1;
D are monovalent moieties which can be the same or different selected from the group consisting of hydrogen, an alkyl group of 1 to about 10 carbon atoms, aryl, and substituted aryl;
R are divalent hydrocarbon groups which can be the same or different;
$R^1$ are monovalent moieties which can be the same or different selected from the group consisting of alkyl, substituted alkyl, aryl, and substituted aryl;
$R^2$ are monovalent moieties which can be the same or different selected from the group consisting of alkyl, substituted alkyl, aryl, and substituted aryl;
$R^3$ are monovalent moieties which can be the same or different selected from the group consisting of alkyl, substituted alkyl, vinyl, aryl, and substituted aryl; and
$R^4$ are monovalent moieties which can be the same or different selected from the group consisting of alkyl, substituted alkyl, vinyl, aryl, and substituted aryl; and
n is an integer of about 300 to about 700;
(b) a polymer or mixture of polymers of the formula

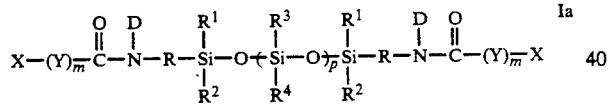

wherein:
p is an integer of about 35 to about 270; and
X, Y, m, D, R, $R^1$, $R^2$, $R^3$, and $R^4$ are as defined above, including sufficient polar solvent to compatibilize the polymers; and
(c) a silicone macromonomer or mixture of silicone macromonomers of the formula

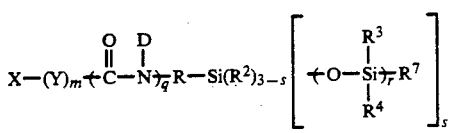

wherein:
q is an integer of 0 to 1;
s is an integer of 1 to 3;
r is an integer of about 35 to about 700;
$R^7$ are monovalent moieties which can be the same or different selected from the group consisting of alkyl, substituted alkyl, alkoxy, alkyl amino, hydroxyl, aryl, and substituted aryl; and
X, Y, m, D, R, $R^2$, $R^3$, and $R^4$ are as defined above.

20. The composition of claim 19 wherein element (a) comprises at least about 10 weight percent of the composition and elements (b) and (c) independently comprise up to about 90 weight percent of the composition.

21. The composition of claim 1, claim 2, or claim 19 wherein
X comprises

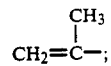

Y comprises

m=1;
D=H;
R comprises —$CH_2CH_2CH_2$—; and
$R^1$, $R^2$, $R^3$, and $R^4$ each comprise —$CH_3$.

22. The composition of claim 1, claim 2, or claim 19 wherein
X comprises $CH_2$=CH—;
Y comprises

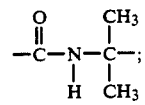

m=1;
D=H;
R comprises —$CH_2CH_2CH_2$—; and
$R^1$, $R^2$, $R^3$, and $R^4$ each comprise —$CH_3$.

23. The composition of claim 1, claim 2, or claim 19 wherein
X comprises $CH_2$=CH—;
m=0;
D=H;
R comprises —$CH_2CH_2CH_2$—; and
$R^1$, $R^2$, $R^3$, and $R^4$ each comprise —$CH_3$.

24. A composition which is curable to a pressure sensitive adhesive comprising:
(a) the composition of claim 19; and
(b) sufficient tackifier to endow the cured composition with adhesive tack at the use temperature.

25. The composition of claim 19 which further comprises at least one of the additives selected from the group consisting of a free radical initiator, a filler, and a nonpolar solvent.

26. The composition of claim 24 which further comprises at least one of the additives selected from the group consisting of a free radical initiator, a filler, and a nonpolar solvent.

27. An elastomer formed from the radiation curing of the composition of claim 19 or 25.

28. A pressure sensitive adhesive formed from the radiation curing of the composition of claim 24 or 26.

29. A method of preparing a silicone macromonomer of the formula

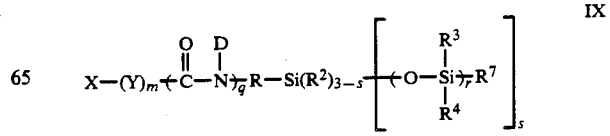

wherein:
q ia an integer of 0 to 1;
s is an integer of 1 to 3;
r is an integer of about 35 to about 700;
$R^7$ are monovalent moieties which can be the same or different selected from the group consisting of alkyl, substituted alkyl, alkoxy, alkyl amino, hydroxyl, aryl, and substituted aryl;
X is a monovalent moiety having ethylenic unsaturation;
Y is a divalent linking group;
m is an integer of 0 or 1;
D is a monovalent moiety selected from the group consisting of hydrogen, an alkyl group of 1 to about 10 carbon atoms, aryl, and substituted aryl;
R is a divalent hydrocarbon group;
$R^2$ are monovalent moieties which can be the same or different selected from the group consisting of alkyl, substituted alkyl, aryl, and substituted aryl;
$R^3$ are monovalent moieties which can be the same or different selected from the group consisting of alkyl, substituted alkyl, vinyl, aryl, and substituted aryl; and
$R^4$ are monovalent moieties which can be the same or different selected from the group consisting of alkyl, substituted alkyl, vinyl, aryl, and substituted aryl;

which comprises the step of:
reacting a fluorosilane terminating agent represented by the formula

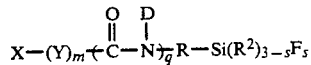

wherein:
X, Y, m, D, q, R, $R^2$ and s are as defined above, with a solution of living polymeric siloxanolate in a suitable non-hydroxylic solvent in order to form said silicone macromonomer.

30. The silicone macromonomer made in accordance with the method of claim 29.

* * * * *

UNITED STATES PATENT AND TRADEMARK OFFICE
CERTIFICATE OF CORRECTION

PATENT NO. : 5,091,483

DATED : February 25, 1992

INVENTOR(S) : Mieczyslaw H. Mazurek, Steven S. Kantner, Charles M. Leir, Yvan A. Bogaert, Robert K. Galkiewicz, and Audrey A. Sherman It is certified that error appears in the above-identified patent and that said Letters Patent is hereby corrected as shown below:

Col. 18, line 41    "$\frac{(MW)_{mr,1}}{(M_n)}$" should read    --$\frac{(MW)}{(\overline{M}_n)}$--

Col. 21, line 58    "$\frac{(MW)_{mr,1}}{(M_n)}$" should read    --$\frac{(MW)}{(\overline{M}_n)}$--

Col. 27, line 47    "Darocur TM 1173" should read --Darocur™ 1173.--

Col. 28, line 8    "Lupersol TM 554M75" should read --Lupersol™ 554M75.--

Col. 28, line 57    "0 1 g" should read --0.1 g--

Col. 28, line 67-68    "1 4 g" should read --1.4 g--

Signed and Sealed this

Nineteenth Day of October, 1993

Attest:

BRUCE LEHMAN

*Attesting Officer*     *Commissioner of Patents and Trademarks*